(12) United States Patent
Faubert et al.

(10) Patent No.: US 9,566,029 B2
(45) Date of Patent: Feb. 14, 2017

(54) METHOD AND DEVICE FOR ASSESSING, TRAINING AND IMPROVING PERCEPTUAL-COGNITIVE ABILITIES OF INDIVIDUALS

(75) Inventors: Jocelyn Faubert, Montreal (CA); David Tinjust, Saint-Laurent (CA)

(73) Assignee: COGNISENS INC., Montreal, Quebec (CA)

( * ) Notice: Subject to any disclaimer, the term of this patent is extended or adjusted under 35 U.S.C. 154(b) by 0 days.

(21) Appl. No.: 13/121,623

(22) PCT Filed: Sep. 29, 2009

(86) PCT No.: PCT/CA2009/001379
§ 371 (c)(1),
(2), (4) Date: Aug. 15, 2011

(87) PCT Pub. No.: WO2010/037222
PCT Pub. Date: Apr. 8, 2010

(65) Prior Publication Data
US 2011/0300522 A1    Dec. 8, 2011

Related U.S. Application Data

(60) Provisional application No. 61/136,751, filed on Sep. 30, 2008.

(51) Int. Cl.
*G09B 5/02* (2006.01)
*A61B 5/16* (2006.01)
(Continued)

(52) U.S. Cl.
CPC . *A61B 5/16* (2013.01); *G09B 5/02* (2013.01); *G09B 9/00* (2013.01); *H04N 13/0438* (2013.01);
(Continued)

(58) Field of Classification Search
USPC ......................................................... 434/236
See application file for complete search history.

(56) References Cited

U.S. PATENT DOCUMENTS 4,962,420 A * 10/1990 Judenich ..................... 348/744
6,271,808 B1 * 8/2001 Corbin ........................... 345/7
(Continued)

FOREIGN PATENT DOCUMENTS

CA    2667315    5/2008
CN    101067716    11/2007
(Continued)

OTHER PUBLICATIONS

Allen, R., P. McGeorge, et al. (2006). Multiple-target tracking: A role for working memory? Q J Exp Psychol (Colchester), 59: 6, pp. 1101-1116.
(Continued)

*Primary Examiner* — James Hull
(74) *Attorney, Agent, or Firm* — BCF LLP

(57) ABSTRACT

A device and method for evaluating or improving perceptual-cognitive abilities of a subject, comprising displaying virtual objects moving in a given three-dimensional environment during successive tests. The subject is in visual contact with the virtual objects moving in the three-dimensional environment, and the speed of movement of the virtual objects in the three-dimensional environment during the successive tests is changed.

16 Claims, 15 Drawing Sheets

(51) Int. Cl.
*G09B 9/00* (2006.01)
*H04N 13/04* (2006.01)
*A61B 5/00* (2006.01)

(52) U.S. Cl.
CPC ...... *H04N 13/0459* (2013.01); *H04N 13/0468* (2013.01); *A61B 5/7445* (2013.01); *G09G 2320/0261* (2013.01)

(56) References Cited

U.S. PATENT DOCUMENTS

| | | | |
|---|---|---|---|
| 6,425,764 B1* | 7/2002 | Lamson | 434/236 |
| 6,437,777 B1* | 8/2002 | Kamachi et al. | 345/419 |
| 6,896,655 B2* | 5/2005 | Patton et al. | 600/300 |
| 8,016,416 B1* | 9/2011 | Straus | 351/200 |
| 8,154,473 B2* | 4/2012 | Engel et al. | 345/4 |
| 2005/0216243 A1 | 9/2005 | Graham et al. | |
| 2005/0270367 A1 | 12/2005 | McDowall et al. | |
| 2007/0004513 A1* | 1/2007 | Wells et al. | 463/31 |
| 2007/0048702 A1 | 3/2007 | Jang et al. | |
| 2007/0166675 A1* | 7/2007 | Atkins et al. | 434/236 |
| 2007/0196809 A1* | 8/2007 | Sen | 434/365 |
| 2007/0218440 A1* | 9/2007 | Delahunt et al. | 434/236 |
| 2007/0293735 A1 | 12/2007 | Chan et al. | |
| 2008/0161080 A1* | 7/2008 | Terasaki et al. | 463/9 |
| 2008/0280276 A1* | 11/2008 | Raber et al. | 434/236 |
| 2009/0046140 A1* | 2/2009 | Lashmet et al. | 348/51 |
| 2009/0111073 A1* | 4/2009 | Stanley | 434/21 |
| 2009/0295683 A1* | 12/2009 | Pugh et al. | 345/9 |
| 2010/0255449 A1* | 10/2010 | Fadde | 434/236 |

FOREIGN PATENT DOCUMENTS

| | | |
|---|---|---|
| CN | 101231790 | 7/2008 |
| CN | 101246600 | 8/2008 |
| KR | 20030007776 | 1/2003 |
| KR | 20090014321 | 2/2009 |
| WO | 2006086504 | 8/2006 |
| WO | 2009049404 | 4/2009 |

OTHER PUBLICATIONS

Alvarez, G. A. and P. Cavanagh (2005). "Independent resources for attentional tracking in the left and right visual hemifields." Psychol Sci 16(8): 637-43.

Alvarez, G. A. and S. L. Franconeri (2007). "How many objects can you track? Evidence for a resource-limited attentive tracking mechanism." J Vis 7(13): 14 1-10.

Bruggeman, H., A. Yonas, et al. (2007). "The processing of linear perspective and binocular information for action and perception." Neuropsychologia 45(7): 1420-6.

Cavanagh, P. and G. A. Alvarez (2005). "Tracking multiple targets with multifocal attention." Trends Cogn Sci 9 (7): 349-54.

Horowitz, T. S., R. S. Birnkrant, et al. (2006). "How do we track invisible objects?" Psychon Bull Rev 13(3): 516-23.

Loftus, A., P. Servos, et al. (2004). "When two eyes are better than one in prehension: monocular viewing and end-point variance." Exp Brain Res 158(3): 317-27.

Posner, M. I. (1980). "Orienting of attention." Q J Exp Psychol 32(1): 3-25.

Pylyshyn, Z. (1994). "Some primitive mechanisms of spatial attention." Cognition 50(1-3): 363-84.

Pylyshyn, Z. W. and R. W. Storm (1988). "Tracking multiple independent targets: evidence for a parallel tracking mechanism." Spat Vis 3(3): 179-97.

Scholl, B. J. and Z. W. Pylyshyn (1999). "Tracking multiple items through occlusion: clues to visual objecthood." Cognit Psychol 38(2): 259-90.

Scholl, B. J., Z. W. Pylyshyn, et al. (2001). "What is a visual object? Evidence from target merging in multiple object tracking." Cognition 80(1-2): 159-77.

Sears, C. R. and Z. W. Pylyshyn (2000). "Multiple object tracking and attentional processing." Can J Exp Psychol 54(1): 1-14.

Trick, L. M., T. Peri, et al. (2005). "Age-related differences in multiple-object tracking." J Gerontol B Psycho! Sci Soc Sci 60(2): P102-5.

Viswanathan, L. and E. Mingolla (2002). "Dynamics of attention in depth: evidence from multi-element tracking." Perception 31(12): 1415-37.

Yantis, S. (1992). "Multielement visual tracking: attention and perceptual organization." Cognit Psychol 24(3): 295-340.

Oksama & Hyona (2004). "Is multiple object tracking carried out automatically by an early vision mechanism independent of higher-order cognition? An individual difference approach." Visual Cognition, 11: 5, pp. 631-671.

Trick, L. M. et al (2005). "Multiple-object tracking in children: The "Catch the Spies" task." Cognitive Development, 20, pp. 373-387.

Levitt, H. (1970) "Transformed Up-Down Methods in Psychoacoustics", J. Acoustical Soc. Am., pp. 467-477.

Organized by et al.: "Object Perception, Attention, and Memory 2007 Conference Report 15th Annual Meeting, Long Beach, California, USA", Visual Cognition, vol. 16, No. 1, Jan. 1, 2008, pp. 90-143.

J.C. Piponnier et al.: "Effect of Visual field locus and oscillation frequencies on posture control in an ecological environment", Journal of Vision, vol. 9, No. 1, Jan. 1, 2009, pp. 13-13.

The Supplementary European Search Report issued from the European Patent Office on Jun. 5, 2014.

* cited by examiner

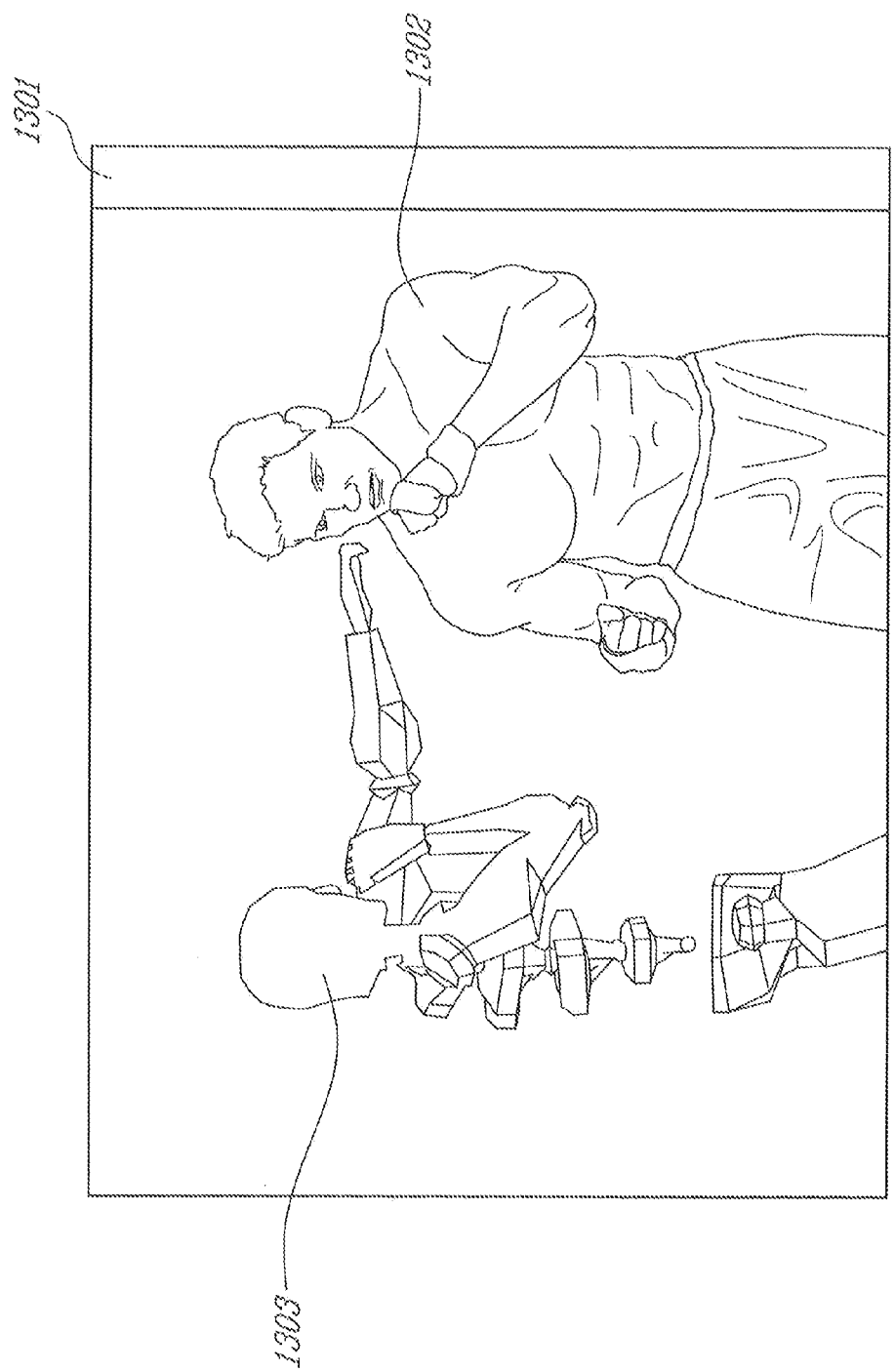

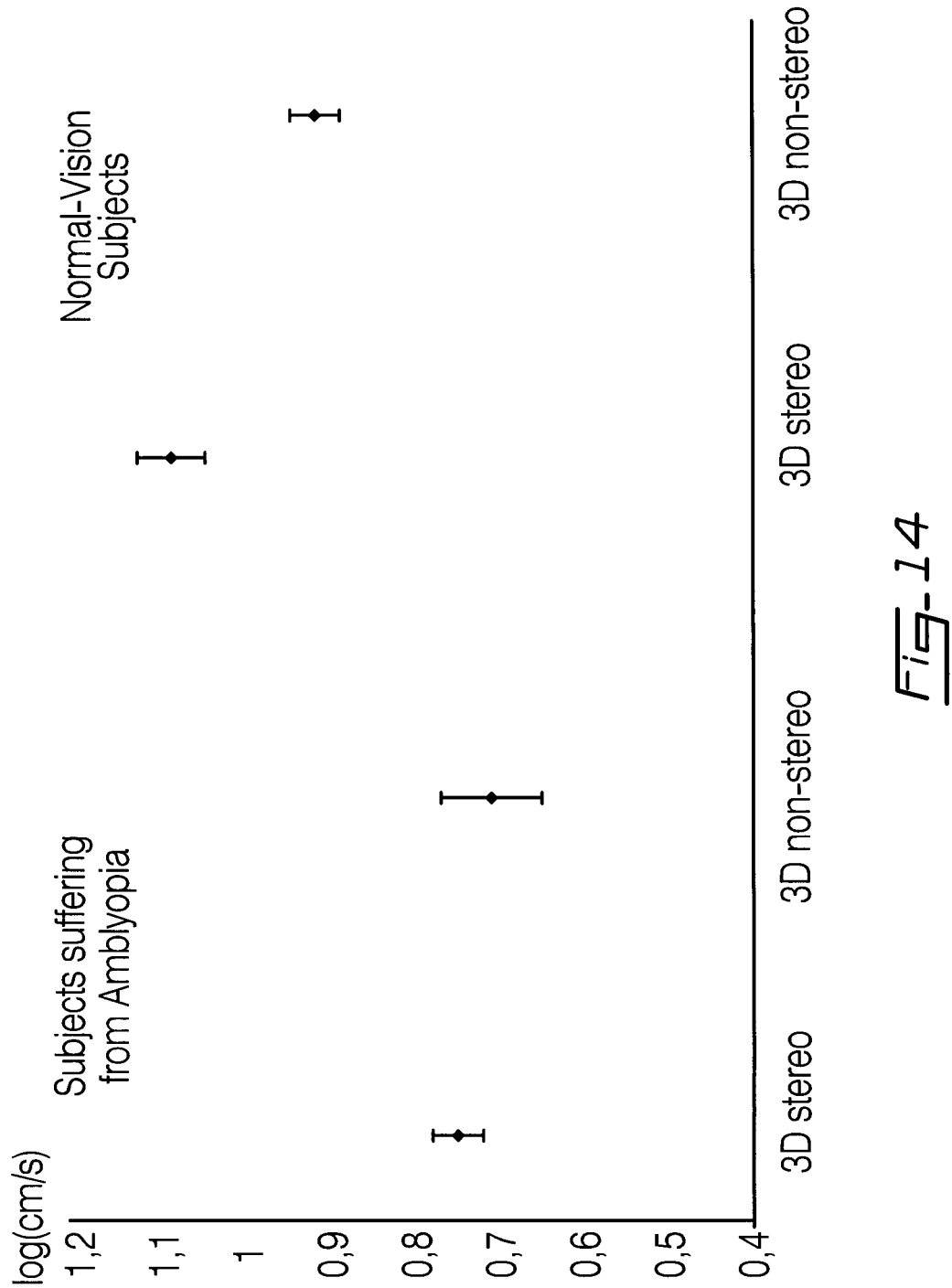

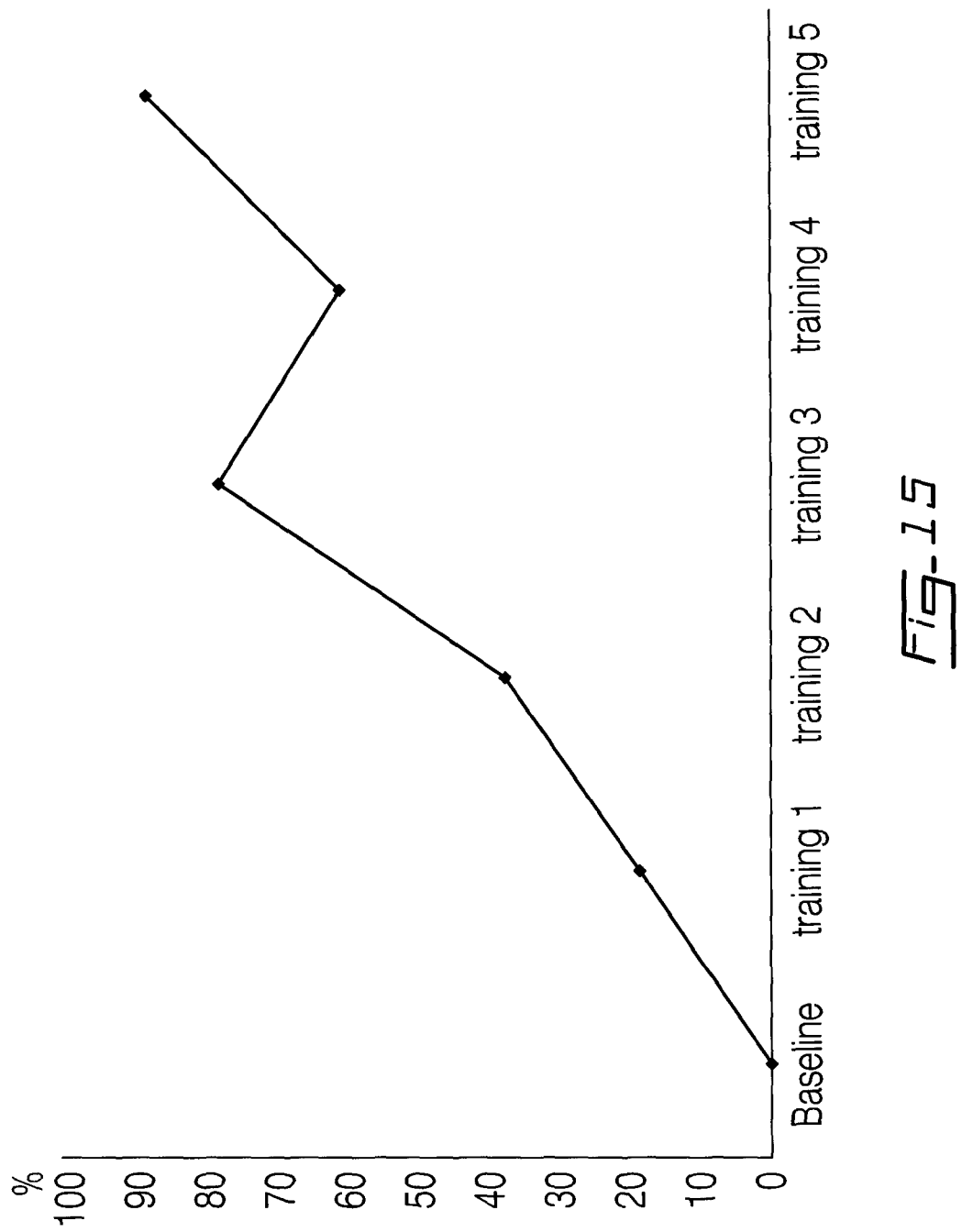

METHOD AND DEVICE FOR ASSESSING, TRAINING AND IMPROVING PERCEPTUAL-COGNITIVE ABILITIES OF INDIVIDUALS

FIELD

The present invention is concerned with the field of perceptual-cognitive abilities of individuals.

BACKGROUND

In everyday life individuals are inexorably exposed to complex visual context in which they concurrently track and integrate multiple moving objects in their visual field. For example, a driver will attend and spatially integrate moving targets such as cars and/or pedestrians. In such environments, perceptual integration of dynamic visual targets is fundamental in order to produce good decision-making processes and appropriate motor responses. Experiments on multiple-object tracking (MOT) ability have demonstrated that attention could be allocated to more than a single focus position contrary to what was generally postulated.

Complete understanding of the mechanisms inherent to MOT is not yet achieved. Different models propose interesting views for a theoretical understanding of the mechanisms involved in this cognitive process.

For example, a first model, the so called FINSTs model, refers to pre-attentive indexes that stick to the moving targets and facilitate attention to assess these indexed objects.

Another example is a grouping model which proposes that during a visual tracking task, the targets are grouped into a single object. The virtual linkage between targets forms the vertices of a deformable polygon which is perceptually integrated while targets move across the visual field.

Finally, a multi-focal model describes the possibility to deploy independent focus of attention on each tracked target.

At an integrative level, a limit concerning the number of tracked moving targets has been previously shown. It appears that young adults are capable to track up to a maximum of five targets. However, it has been shown that this performance decrease during normal aging. It has been shown that elderly people are limited to three items in a MOT task.

At a spatial level and independently of the model considered, a recent study provides new information concerning the early stages of MOT. The results of this study suggest a limited capacity split between the right and left hemifields during the target selection stage. It has been suggested that this hemifield independence is restricted to the very early stage of MOT (selection stage). It has also been suggested that this hemifield specificity could be integrated in a retinotopic frame of reference.

However, at a space representation level and because of their two-dimensional visual space restrictions, classical studies do not take into consideration the stereoscopic power of the visual system that allows better discrimination between the relative positions of multiple objects in space. Also, these approaches do not consider the reality of a 3D (three-dimensional) world where multiple objects move among the three dimensions of space and at different depth positions. Indeed, stereoscopic vision is a higher-level function of our visual system that permits us to have perception of depth and to evaluate if one object is situated before or behind another one in space. At a behavioural level, an individual constantly makes this kind of visual-perceptual judgment whatever the task he/she is involved in. Moreover, the benefits of stereoscopic vision in providing optimal visual cues to control action have already been shown. These studies suggest that the main impact of stereoscopic vision is disambiguating the depth information present in our 3D world in order to produce optimal behaviours. Based on these perception-action interactions, it appears that the evaluation of some specific visual mechanisms is made in environments that simulate in an ecological way the visual-spatial characteristic of our 3D world. Intuitively, this seems to apply to multiple-object tracking which corresponds to a visual-attentional mechanism that could influence many behaviours related to everyday life. However the MOT literature showed that most of the studies evaluate this visual-attentional capacity in experimental protocols restrained in 2D visual space which is drastically different from real-life conditions where tracking people and/or moving objects in crowds or during sports, such as hockey or soccer, is performed in 3D space. Based on these space representation considerations it could be irrelevant to extrapolate the results obtained to real-life tasks.

Moreover, and beyond the space representation consideration, evaluating MOT by estimating the discrete number of elements that can be tracked may not adequately represent subtle individual differences in performance on this cognitive task. Can it be concluded that the integrative capacity of two individuals is equal when both can successfully track four targets? Based on the number of targets tracked, can it be really assumed that two experimental conditions did not differ from each other?

Beyond the limit of the number of objects tracked, there is a need to develop a new approach characterizing sub-parameters that better reflect the efficiency of the attention processes involved in multiple-object tracking.

BRIEF DESCRIPTION OF THE DRAWINGS

In the appended drawings:

FIG. 13 is an illustration of a system for 3D augmented reality used in relation to a boxing ring;

FIG. 14 is a graph showing that the perceptual-cognitive abilities improve with 3D-stereoscopic representation and stereoscopic vision (subjects not suffering from visual amblyopia); and FIG. 15 is a graph showing an example of curve of improvement of the perceptual-cognitive abilities of subjects in relation to the number of training cessions.

DETAILED DESCRIPTION

Figure 1:
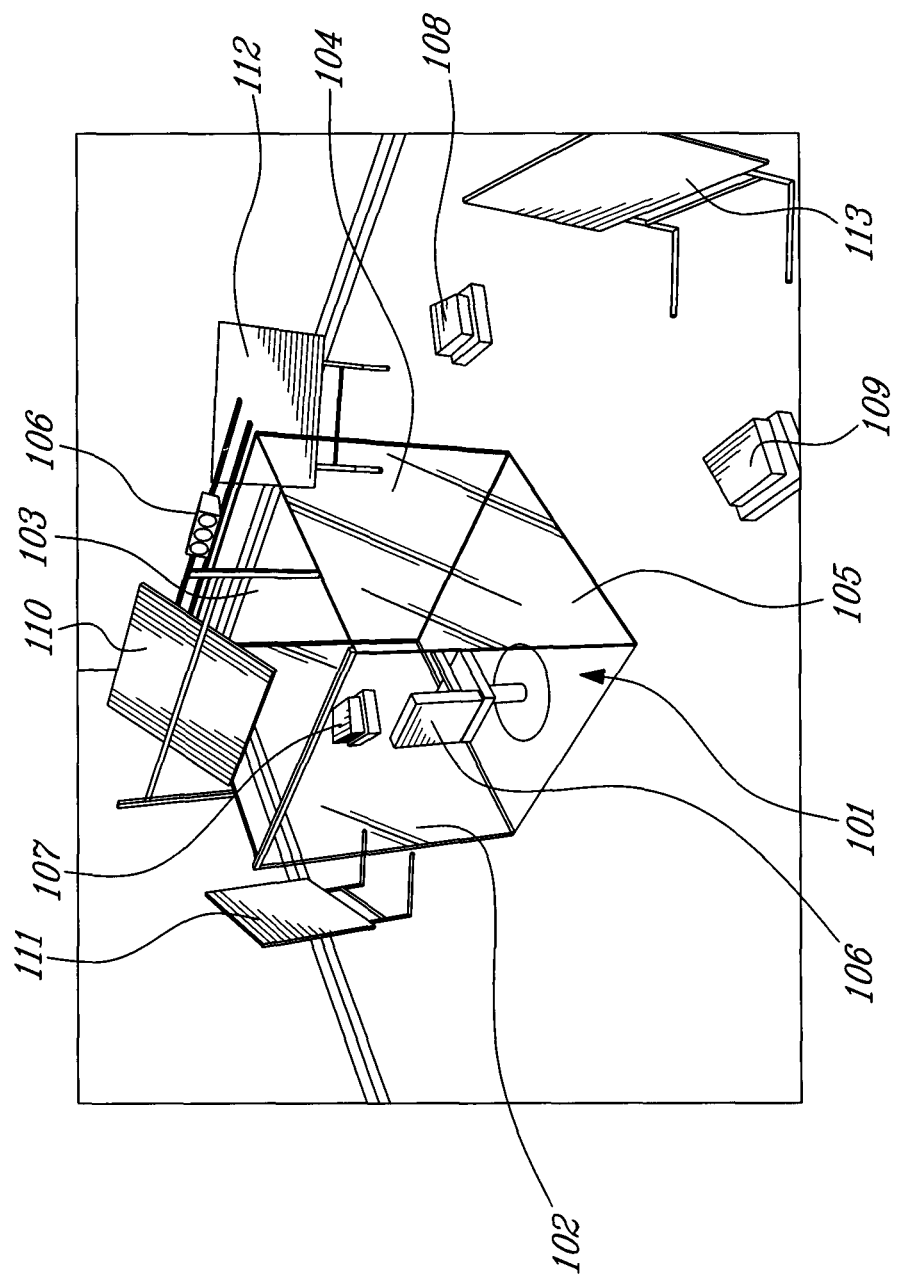
FIG. 1 is a perspective view of an example of full immersive virtual environment.

According to a first aspect of the present invention, there is provided a method of evaluating or improving perceptual-cognitive abilities of a subject, comprising: displaying virtual objects moving in a given three-dimensional environment during successive tests, with the subject in visual contact with the virtual objects moving in the three-dimensional environment; and changing the speed of movement of the virtual objects in the three-dimensional environment during the successive tests. The method may further comprise collecting responses from the subject to the successive tests for use in evaluating, according to an evaluation protocol, the perceptual-cognitive abilities of the subject.

According to a second aspect of the present invention, there is provided a device for evaluating or improving perceptual-cognitive abilities of a subject, comprising: a display of virtual objects moving in a given three-dimensional environment during successive tests, with the subject in visual contact with the virtual objects moving in the three-dimensional environment; and a controller of the display of the virtual objects moving in the given three-dimensional environment during the successive tests, for changing a speed of movement of the virtual objects in the three-dimensional environment. The device may further comprise a collector of responses from the subject to the successive tests for use in evaluating, according to an evaluation protocol, the perceptual-cognitive abilities of the subject.

The foregoing and other objects, advantages and features of the present invention will become more apparent upon reading of the following non-restrictive description of illustrative embodiments thereof, given by way of example only with reference to the accompanying drawings.

As indicated in the foregoing description, beyond the limit of the number of objects tracked, there is a need to develop a new approach characterizing sub-parameters that better reflect the efficiency of the attention processes involved in multiple-object tracking. To achieve this goal, speed-thresholds for a given set of tracked objects using an adaptive protocol (staircase method) can be assessed. To evaluate the capacity of this method to discriminate subtle differences between distinct experimental conditions, the capacity to simultaneously track four targets in two different perceptual contexts is evaluated. More specifically, the MOT speeds under 3D-stereoscopic (SC) and non-stereoscopic (NSC) visual space representations are compared. To be optimally integrated, stereoscopic space representation requires the use of stereoscopic vision whereas this visual capacity is not essential to optimally extract information from a non-stereoscopic visual-scene representation. Such a perceptual comparison could help to both evaluate whether stereoscopic vision optimally drive the processes involved in this kind of cognitive task and the impact of 3D space representation on the processes inherent to MOT. In case of enhanced performance with 3D space representation in individuals with normal stereoscopic vision, this would suggest to modify the conventional 2D-experimental approach.

Embodiment 1

Experiment 1

General Method

Subjects

Ten young adults (5 females; 5 males) participated to this experiment, with ages ranging from 18 to 30 years. All subjects in this and subsequent experiments gave informed consent and reported corrected to normal vision. For Experiments 1, 2 and 3, all subjects were evaluated using a Randot stereotest (Stereo optical Co.) and had normal stereoscopic vision. Participants were also evaluated with a WMS-III Digit spatial-span test (Psychological Corporation) that showed they were capable to retain and immediately recall five items presented within the visual space.

Environment

The device for evaluating or improving perceptual-cognitive abilities of a subject comprises a display of virtual objects moving a given three-dimensional environment during successive tests.

More specifically, the display comprises a fully immersive virtual environment (F.I.V.E.) room 101 (C.A.V.E., Fakespace technology) in which the subject is fully immersed in the given three-dimensional environment and the stimuli are presented (FIG. 1). The fully immersive virtual environment room 101 has a size of, for example, 8×8×8 feet and comprises four (4) projection surfaces (three walls 102, 103 and 104 and a floor 105). The display displays stereoscopic images on the four (4) projection surfaces (the three walls 102, 103 and 104 and floor 105) to form the given three-dimensional environment in which virtual objects are presented. The display comprises, for that purpose, projectors 106, 107, 108 and 109 and associated planar reflectors 110, 111, 112 and 113, respectively to project and display the images on the four (4) projection surfaces (the three walls 102, 103 and 104 and floor 105) under the control of a display controller, for example under the form of a computer (not shown).

The display of the device for evaluating or improving perceptual-cognitive abilities of a subject also comprises a shutter visual implement, for example under the form of liquid crystal shutter stereoscopic goggles (not shown) (Stereographics, San Rafael, Calif.) to enable the subject's 3D stereoscopic perception, more particularly to enable the subject to perceive in 3D the virtual object, the positions of the virtual objects and the three-dimensional environment. Stereoscopic images were rendered with a refresh rate of 48 Hz and the goggles were shuttered at 96 Hz to deliver 48 images per second to the subject's right and left eyes. The display further comprises a positional sensor, for example under the form of a magnetic detector (Flock of birds, Ascension technology corp., Burlington, Vt.) mounted to the goggles in order to track a position of the subject's head. The controller controls the display to correct in real-time a visual perspective relative to the tracked subject's head position. The display controller (for example a "Silicon graphics 540" computer) generates the stimuli and records the subject's responses.

Figure 2:
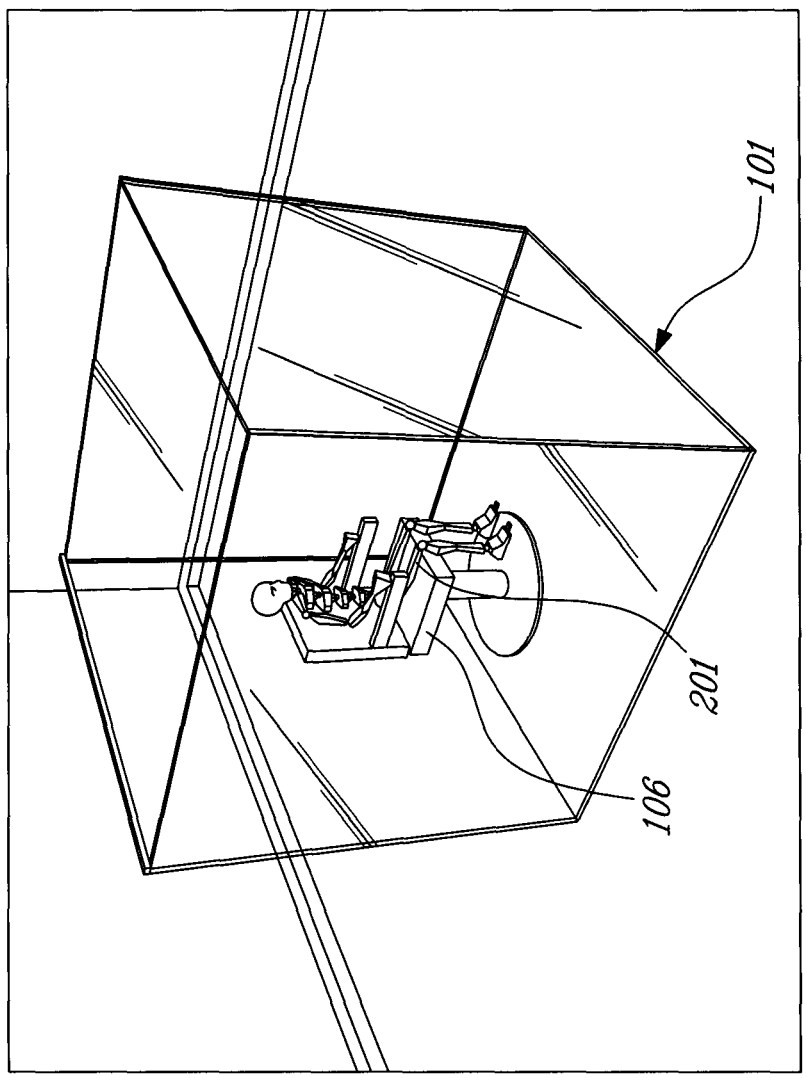
FIG. 2 is a perspective view illustrating the position of a subject in the environment of FIG. 1.

An ophthalmologic chair 106 positioned substantially in a central position of the fully immersive virtual environment (F.I.V.E) room 101 (FIG. 2)) is provided to sit the subject such as 201.

Stimuli

Figure 3:
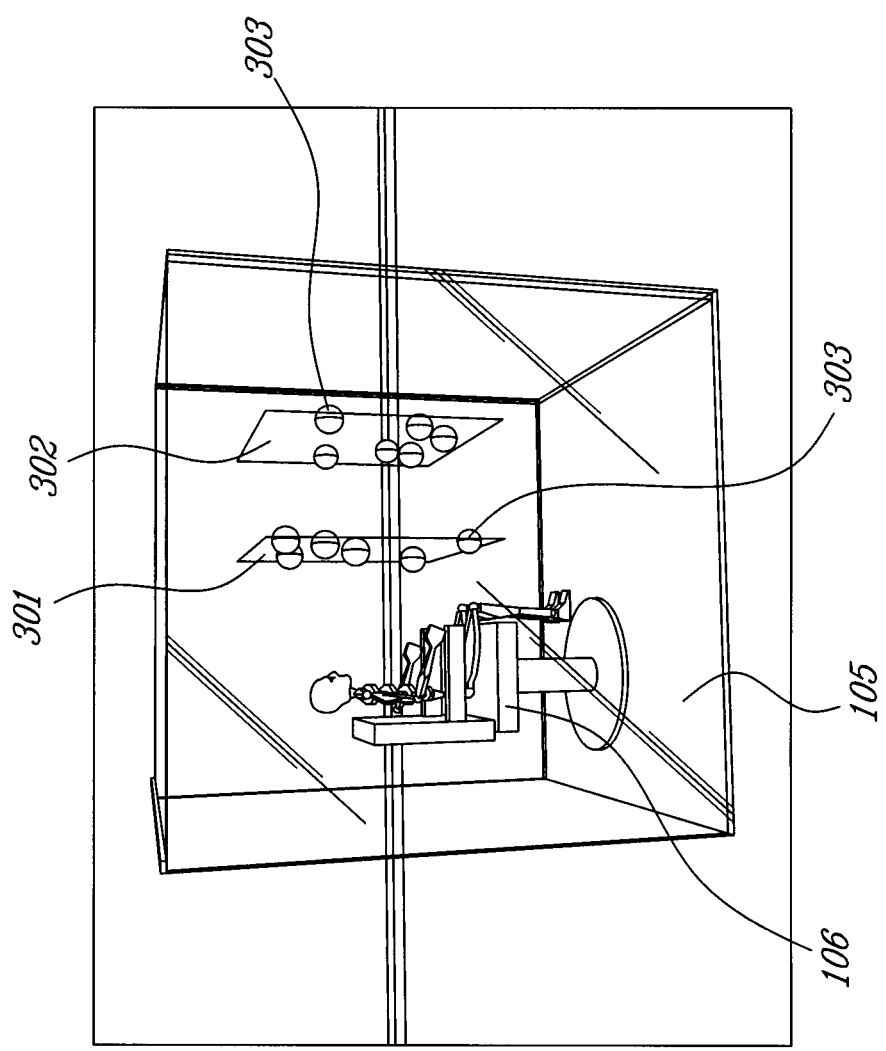
FIG. 3 is a side view illustrating a virtual stimulus presentation in the environment of FIG. 1.
Figure 4:
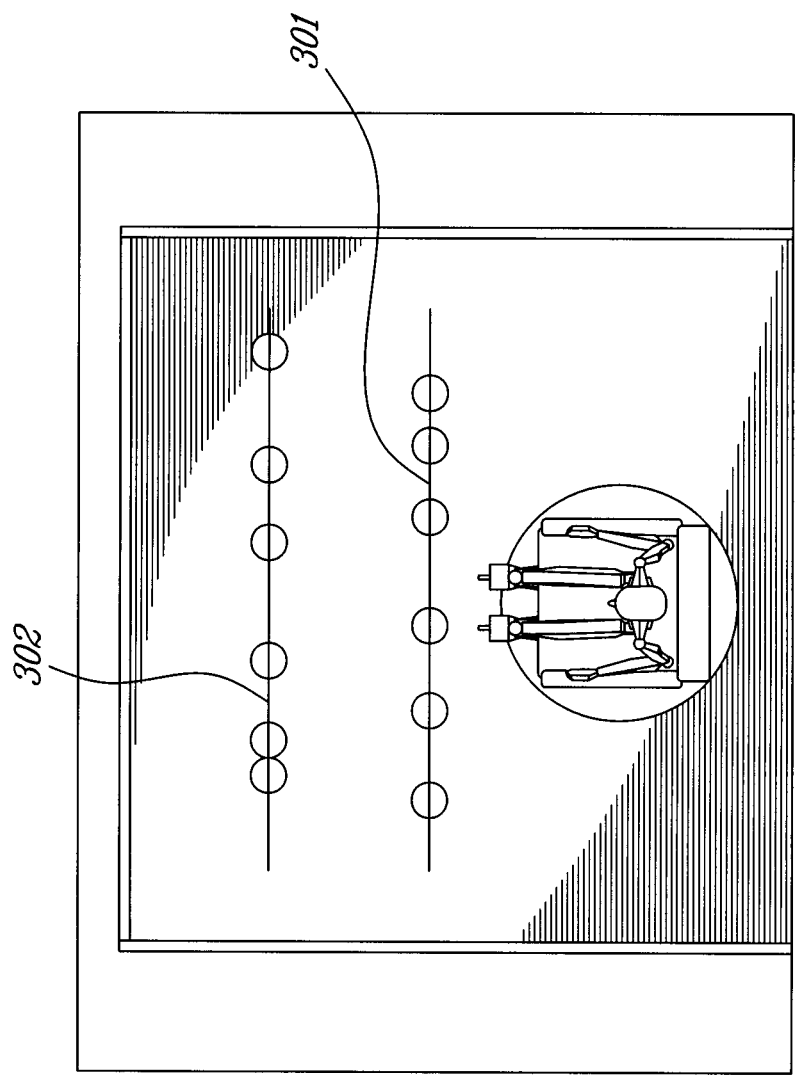
FIG. 4 is a top plan view of the environment of FIG. 1 showing the virtual stimulus presentation of FIG. 3.

As illustrated in FIG. 3, the display of the device for evaluating or improving perceptual-cognitive abilities of a subject displays two (2) virtual transparent planes 301 and 302 and a portion of a number of virtual objects, for example a number of six (6) yellow spheres such as 303 embedded in each plane 301 and 302. It is within the scope of the present invention to display more than two (2) virtual transparent planes. The two (2) parallel, 42° of visual angle planes 301 and 302 are virtually distant from each other by a distance of, for example, 20 centimeters. The controller controls the display to move the corresponding portion of the spheres 303 in each virtual planes 301 and 302 and to present a black fixation spot (not shown) (0.6 degree of visual angle and presented at 67 cm from subject's eyes) substantially in the center of the space between the two (2) transparent virtual planes 301 and 302 (FIGS. 3 and 4). The controller gives, by means of the display, initial random positions to the spheres 303 in the three-dimensional environment at the beginning of each of the successive test. The controller also randomly selects the initial directions of movement of the spheres 303. The controller further controls the display in such a manner that the spheres 303 moving in each virtual plane (301 or 302) collide with each other and with the edges of this virtual transparent plane. The controller also controls the display to move the spheres 303 in each virtual plane (301 or 302) at a constant speed during each test, but to adaptively change the speed of movement of the spheres 303 from one of the successive tests to the other, for example in relation to the responses of the subject.

Within the three (3) Experiments 1, 2 and 3, the subject is in visual contact with the virtual objects, for example the spheres 303, moving within their respective virtual transparent planes (301 or 302) in the three-dimensional environment, and the controller controls the display to execute, during each test, the following sequence of phases:

Presentation phase: Six (6) yellow spheres 303 are presented to the subject in each plane (301 or 302) for 2.5 seconds, in random positions, and with a spatial restriction of 2 centimeters between the spheres 303.

Indexation phase: Two (2) spheres in each plane (301 or 302) turn red for 2 seconds to be identified as target spheres by the subject. Then, these four (4) spheres return to their initial colour (yellow).

Tracking phase: All the spheres 303 move for 6 seconds while the target spheres are tracked by the subject. After the duration of 6 seconds, the movement of the spheres 303 is stopped. During the period of 6 seconds, the spheres 303 embedded in each virtual transparent plane (301 or 302) are enabled to collide with each other and the edges of the virtual transparent plane (301 or 302).

Response phase: In this phase, each sphere 303 is associated to a number from 1 to 12, and the subject verbally identifies, as response to the test, the spheres 303 formerly identified as target spheres.

Figure 5:
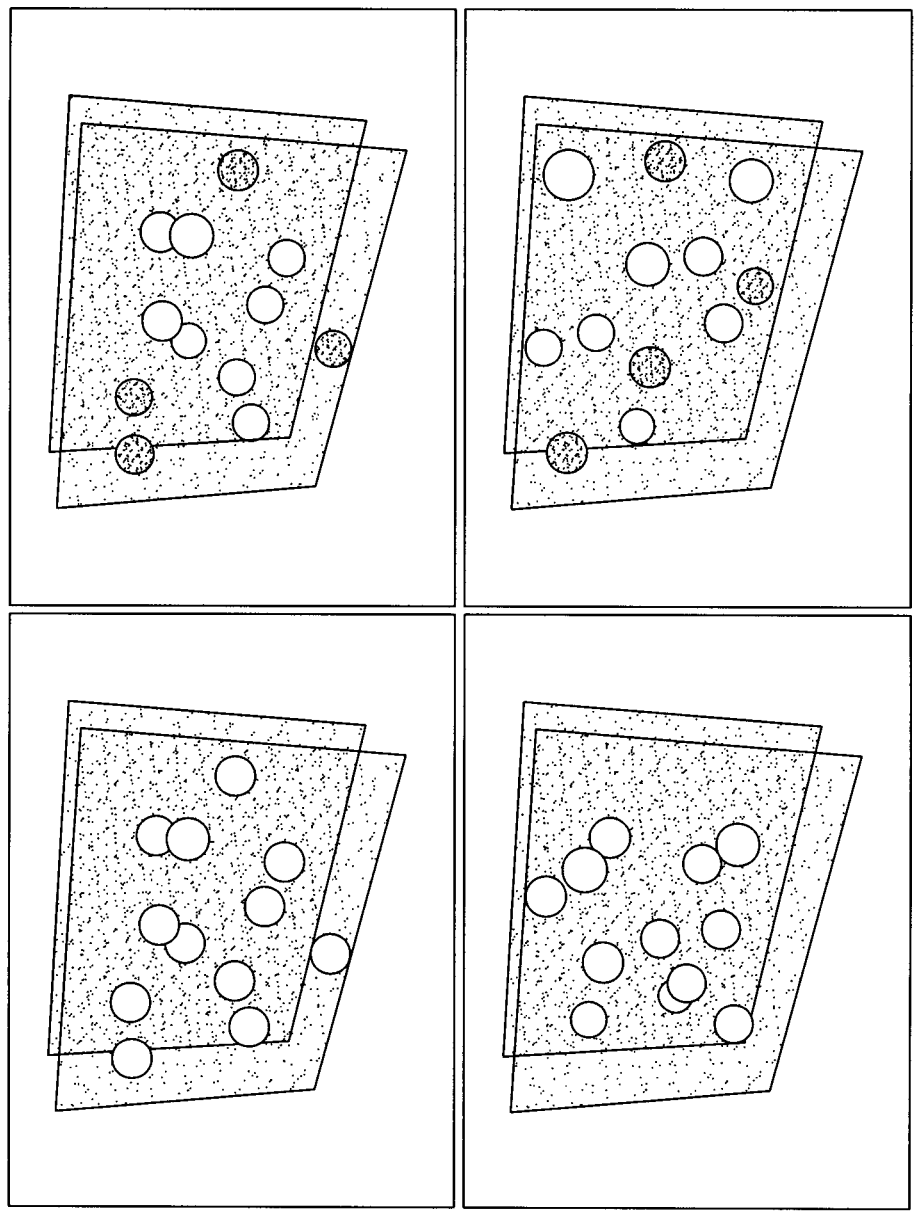
FIG. 5 are perspective views illustrating a sequence of MOT tasks.

Feedback phase: Following the response phase, the four (4) spheres formerly identified as target spheres turn red for 3 seconds to give feedback to the subject (FIG. 5).

Perceptual Conditions

The controller controls the display to conduct the successive tests in one of the following two (2) perceptual conditions. A first perceptual condition consists of a 3D-stereoscopic condition (SC) in which stereoscopic projection presents slightly different images to the subject's eyes to induce 3D perception, more specifically to allow subject's stereoscopic vision and give to the subject a perception of depth; the subject then perceives the two (2) planes separated by a space where the black fixation spot is presented. A second perceptual condition consists of a non-stereoscopic condition (NSC) in which the same image is presented to each eye of the subject to prevent subject's stereoscopic vision and perception of depth. In the second NSC perceptual condition, the two virtual planes 301 and 302, the twelve (12) spheres 303, and the black fixation spot are perceived as integrated into a same virtual plane.

Speed Variation

In one embodiment, the controller of the device for evaluating or improving perceptual-cognitive abilities of a subject may control the display to produce a staircase variation (up or down) of the speed of the spheres 303 moving in the respective planes 301 or 302 from one of the successive tests to the other. By means of the display, the controller adjusts the speed of the spheres 303 from one test to the other in relation to the responses of the subject to the successive tests. For example, the initial speed of movement of the spheres 303 is 2.5 cm/s. Good answer is considered as the identification of the four (4) target spheres. All other responses are considered as wrong. The staircase speed variation can be set with eight (8) inversions. For example:

Before the second inversion, the speed of the spheres 303 is increased (good answer) or decreased (wrong answer) by a factor of 0.2 log unit at each test;

From the second inversion to the fourth inversion, the speed of the spheres 303 is increased (good answer) or decreased (wrong answer) by a factor of 0.1 log unit at each test;

Afterwards, the speed of the spheres 303 is increased (good answer) or decreased (wrong answer) by a factor of 0.05 log unit at each test.

Procedure

Subjects sit on the ophthalmologic chair 106. The chair height is adjusted in order to adjust subject's gaze at 57 cm from the black fixation spot and 160 cm from the floor 105 (FIG. 3). The subjects are asked to focus their gaze on the fixation spot while tracking the four (4) spheres 303 identified as target spheres moving in the virtual transparent planes 301 and 302.

A first alternative of collector of subject's responses consists of a computer (not shown) in which the experimenter enters, following each of the successive tests, verbal responses from the subject identifying the four (4) spheres 303 that he/she considers to be the target spheres. Knowledge of result is then visually provided to the subject (the four (4) spheres 303 formerly identified as target turn red). The initial perceptual condition (SC or NSC) was randomly chosen and the successive perceptual conditions were counterbalanced. In each perceptual condition, the subject's performance is calculated by averaging results obtained on six (6) speed threshold sessions.

According to a second alternative, the collector of subject's responses may comprise a device, such as a keyboard, real or virtual, operated by the subject to enter in the computer their responses to the successive tests identifying the four (4) spheres 303 that he/she consider to be the target spheres. A third alternative of collector of subject's responses would be a voice recognition system to enter verbal responses from the subject to the successive tests in the computer.

Then, the computer is programmed to interpret the subject's responses to the successive tests, and present results using a suitable protocol adapted to evaluate the perceptual-cognitive abilities of the subject. In particular, this protocol uses the responses of the subject to the particular events or situations as a function of the speed of movement of the virtual objects in the three-dimensional environment to evaluate the perceptual-cognitive abilities of the subject.

Results

After each experiment, the subject was asked in which condition (stereoscopic or non-stereoscopic) it was easier to perform. Two (2) out of the ten (10) subjects felt that the NSC perceptual condition was easier to perform than the SC perceptual condition even if their performance was better in the SC condition. The other eight (8) subjects subjectively felt that their performance was higher in the SC condition and it was the case when analysing their results.

Statistical analysis was achieved by a student paired T-test and significant results were considered when the p-value did not reach 0.05. The statistical analysis of the results has shown that the speed-thresholds obtained in the SC condition were significantly higher than those obtained in the NSC condition, t (1, 9)=7.242, p=0.000.

Figure 6:
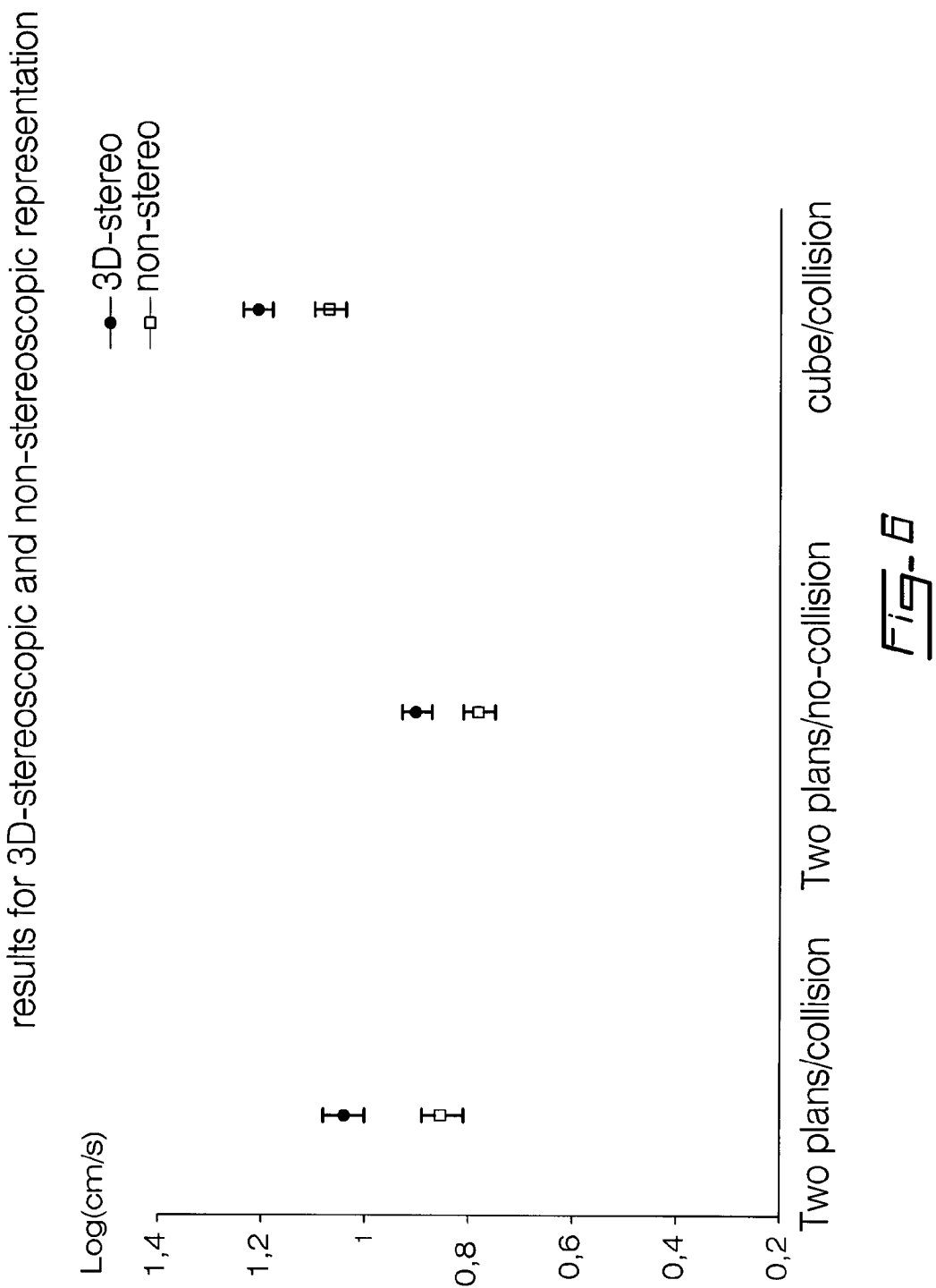
FIG. 6 is a graph showing results for 3D stereoscopic and non-stereoscopic representation during the experiments.

More specifically, the speed-thresholds in the SC condition were higher than in the NSC condition by a factor of 1.49 (FIG. 6, left data).

Discussion

Experiment 1 quantifies the 3D-stereoscopic space representation advantage in MOT. This better performance is characterized by significant higher speed-thresholds. These higher thresholds imply that the capacity to track four (4) simultaneous targets is enhanced when a better disambiguating separation between planes is permitted by the availability of 3D-stereoscopic space representation of the visual scene. These results suggest, for individuals with normal stereoscopic vision, a better extraction and segregation of the pertinent visual information when 3D-stereoscopic space representation is available.

Alternatively, a methodological parameter of Experiment 1 could potentially influence these results. In the experimental set-up, the moving spheres presented in each virtual plane could collide between themselves and with the virtual edge of their respective plane. In the 3D-stereoscopic (SC condition) condition this collision parameter could not have any consequences at a perceptual level. However, in the non-stereoscopic condition (NSC condition) all the elements of the visual scene were perceived as integrated within a unique plan and half of the spheres could collide between each other while pass through the other six remaining ones. Because of this consideration, it could result some perceptual incertitude or confusion related to the NSC condition. This perceptual difference between the SC and NSC conditions could potentially generate the significant advantage obtained in the performance recorded in the SC condition. To evaluate if the results obtained between the two perceptual SC and NSC conditions in Experiment 1 would be attributed to the collision parameter and the confusing effect that it would generate in the NSC condition, a second experiment (Experiment 2) was elaborated. In Experiment 2, the controller controls the display in such a manner that the virtual spheres 303 moving in each virtual plane 301 or 302 cannot collide but pass through each other in the two perceptual conditions (SC and NSC).

Experiment 2

Ten naive young adults (5 females; 5 males) participated to this experiment (ages ranging from 18 to 30 years old). In Experiment 2, the same set-up and procedure as in Experiment 1 was used with the difference that there was no collision between the spheres 303; only collision of the spheres 303 with the edges of the planes 301 and 302 were kept. This means that independently of the perceptual condition (SC or NSC conditions) the spheres 303 pass through each other and avoid the potential confusing effect that was generated during the NSC condition in Experiment 1.

Results

Subjective feeling relative to the perceptual condition have shown that three (3) of the ten (10) participants felt that the NSC condition was easier to perform than the SC condition even if their performance was better in the SC condition. The other remaining seven (7) participants subjectively felt that their performance was higher in the SC condition and that was the case when contrasted with their results.

A paired T-test analysis revealed that the speed thresholds obtained in the SC condition were significantly higher than those obtain in the NSC condition, t (1, 9)=4.995, p=0.001. Similarly to the results obtained in Experiment 1, the speed thresholds were higher (by a factor of 1.29) in the SC condition than in the NSC condition (see FIG. 6, middle data). This invalidates the possibility that the higher speed-thresholds obtained in the SC condition of Experiment 1 were the consequence of a confusing effect induced by the fusion of the two planes 301 and 302 that made half of the spheres collide with each other but pass through the other six (6) remaining spheres 303.

Discussion

The results obtained in Experiment 2 confirm that 3D-stereoscopic space representation optimally improves the perceptual-cognitive processes involved in a multi-element tracking task. The data contrasting the speed-thresholds in the multiple-object tracking task for the 3D-stereoscopic vision space representation and the non-stereoscopic space representation have shown the benefit to integrate visual information in a stereoscopic manner. Contrary to the results obtained in non-stereoscopic condition, it clearly appears that individuals could attend to target at higher speed in the 3D-stereoscopic space representation. This suggests the power of stereoscopic vision to disambiguate or to segregate location of objects when attention has to be allocated at planes of different depths relative to tracked objects.

From the data obtained in the first two experiments (Experiments 1 and 2), it seems that speed-threshold appears to be a reliable measure to evaluate performance in a multiple object tracking task. Also, the results have shown that beyond the number of objects being tracked, a speed-threshold protocol allows to evaluate the MOT performance in a more precise manner.

Experiment 3

The objective of this experiment was to determine the effect of evaluating MOT mechanisms in more ecological conditions allowing the transposition of the results to real life context. In Experiment 3, speed-threshold in a set-up where the tracked virtual objects are constrained in a virtual volume was assessed. This condition allows perception of depth and movement of the virtual objects in the three (3) spatial dimensions (x, y and z axes) as this is the case in the 3D real world.

Figure 7:
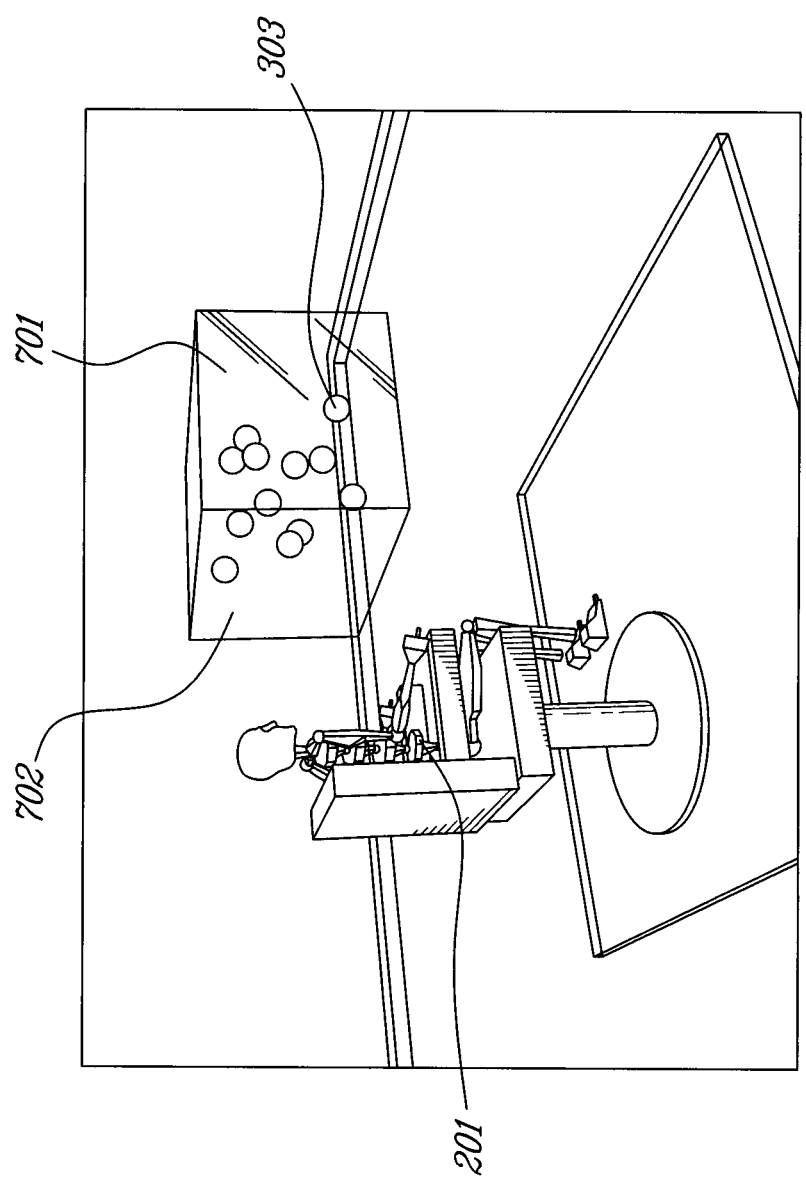
FIG. 7 is a perspective view showing a transparent virtual volume containing objects as presented to a subject.

Ten naive young adults (5 females; 5 males) participated to Experiment 3 (ages ranging from 18 to 30 years old). In Experiment 3, the same procedure and method as in Experiment 1 was used with the exception that the controller controlled the display to display in the three-dimensional environment a three-dimensional volume, for example a three-dimensional virtual, transparent cube 701, in which the virtual objects, for example the virtual spheres 303, are confined and move in three spatial dimensions (FIG. 7). In Experiment 3, the virtual cube 701 had, as a non limitative example, sides of 44 cm.

The anterior side 702 of the cube 701 measures 42° of visual angle and is seen by the subject at a distance of 57 cm. The center of the cube 701 is virtually positioned at 79 cm from the subject's eyes. The sides and edges that compose the cube 701 are transparent. The controller controls the display in such a manner that (a) the twelve (12) spheres 303 moving within the cube 701 collide with each other within the spatial limits imposed by the virtual transparent cube 701. The controller also controls the display in such a manner that the twelve (12) spheres 303 moving within the cube 701 collide with the edges and sides of the cube 701. The same perceptual conditions than in Experiment 1 (3D-stereoscopic condition (SC) and non-stereoscopic condition (NSC)) are used for visually presenting the 3D scene. This means that, in the SC condition, the spheres 303 move in a virtual volume along the x, y and z axes whereas, in the NSC condition, the spheres 303 are embedded in a single plane in which the 3D scene is seen under a perspective view. In this NSC condition, the z-axis displacements are represented by monocular indices; the sides of the spheres 303 expand or constrict relative to the antero-posterior displacement. In Experiment 3, the speed of the virtual spheres 303 cannot be compared to the speed generated in the first two Experiments 1 and 2. The reason is that, in Experiment 3, the speed vector is distributed along the three (3) axes (x, y and z) to induce a lower speed perception by the subject 201. This distribution of speed in the three (39) spatial dimensions potentially generates artificial higher speed-thresholds than in the first two (2) Experiments 1 and 2 in which speed-vectors were generated in two (2) spatial dimensions, more specifically along axes x and y.

Results

Subjective feeling relative to the perceptual conditions has shown that three (3) out of the ten (10) subjects felt that the NSC condition was easier to perform than the SC condition even if their performance was better in the SC condition. The other seven (7) remaining subjects subjectively felt that their performance was higher in the SC condition and that was the case when contrasted with their results.

The paired T-test analysis showed that the speed-thresholds obtained in the SC condition were significantly higher than those obtained in the NSC condition, $t(1, 9)=5.949$, $p=0.000$. In the same manner as in the first two (2) Experiments 1 and 2 the results have shown the advantage to perform MOT task within a 3D-stereoscopic condition. Such advantage is characterized by higher speed-thresholds in the SC condition versus the NSC condition (with a factor of 1.42; see left data in FIG. 6).

The above results confirm the positive impact of the 3D-stereoscopic perceptual condition on the measured speed-thresholds and suggest the advantage of using ecological space representations to evaluate MOT performance. These higher speed-thresholds obtained in the 3D-stereoscopic condition also confirm that the use of 3D-stereoscopic space representations optimize the extraction of pertinent information necessary to the subject for an efficient simultaneous tracking of multiple objects in space.

General Discussion

In the foregoing description, speed-thresholds are used to subtly measure the performance of subjects during multiple-object tracking tasks. In fact, the aim is to assess whether this type of measure can subtly differentiate the performance of two (2) subjects that can both track the same number of target objects during a MOT experiment. The data obtained during the three (3) Experiments 1, 2 and 3 clearly show that subjects are capable to track four (4) moving target objects. Also, the results have shown that, for a same number of target objects being tracked and within a given group of subjects, the subjects' performance subtly varies in terms of speed-threshold and relative to the perceptual condition (for example SC or NSC) they are exposed to. This reflects the possibility to deeper investigate this kind of cognitive task and suggests that multiple-object tracking evaluation takes advantage of considering these potential inter-individual differences that could reflect differences at an integrative level.

The above investigations permit to evaluate whether 3D-stereoscopic perceptual condition gives an advantage, during a MOT task, to subjects with normal stereoscopic vision. It is also possible to assess whether 3D-stereoscopic visual information is the optimal substrate to segregate information necessary to correctly attend to objects located at different depth during a MOT task or whether monocular visual indices (non-stereoscopic perceptual condition) is sufficient to optimally drive this visual-perceptual cognitive mechanism. Experiments 1 and 2 show that, when target objects are visually presented in a 3D-stereoscopic condition, the speed-thresholds obtained are higher than when the visual information is presented in a non-stereoscopic condition. These results suggest that stereoscopic visual indices optimize the extraction and the integration by the visual system of the pertinent spatial elements that optimally drive the mechanisms inherent to a multiple-object tracking task. This is confirmed by Experiment 3 in which the task is performed in a virtual volume that replicates the 3D reality of our world. These results are summarized in FIG. 6 and show approximately the same advantage of 3D-space representation in Experiments 1, 2 and 3. The graph of FIG. 6 shows that the advantage obtained results from the 3D-space representation and not from other experimental parameters. Taken together, the results obtained in Experiments 1, 2 and 3 strongly argue for a major implication of 3D-stereoscopic visual representation in the optimal functioning of the processes involved during multiple-object tracking.

The results of Experiments 1, 2 and 3 show that the use of 3D-stereoscopic perceptual condition in the integrative mechanisms involved in MOT is advantageous. This advantage of 3D-stereoscopic perceptual condition could be the consequence of an internal 3D representation of the environment that leads to optimal integration when visual information is displayed in a 3D manner. Independent from the model considered and of the different spatial and integrative limits described for MOT, space representation within a 3D internal frame of reference is an important characteristic of the mechanism involved in MOT. This means that target indexation and tracking are optimally driven when 3D-stereoscopic indices are available.

Conclusions

It appears that integrative mechanisms linked to MOT are optimally driven within a 3D-stereoscopic perceptual condition or space representation. This could result from a natural proclivity of the brain to represent the environment in a volumetric or 3D manner. This also suggests that, to optimally and relevantly assess multiple-object tracking capacity and to infer results to real-life situations like driving or other complex dynamic visual contexts, it is necessary to evaluate this visual-attentional capacity in perceptual conditions that conform to the visual-spatial reality of our world. Accordingly, 3D-stereoscopic perceptual condition or space representation appears as an advantageous parameter to integrate in multiple-object tracking protocols.

Also, a speed-thresholds measure constitutes a precise and reliable procedure to discriminate the visual-attentional limits of subjects within the experimental conditions in MOT.

Embodiment 2

Three-Dimensional Visual Immersion

Figure 8:
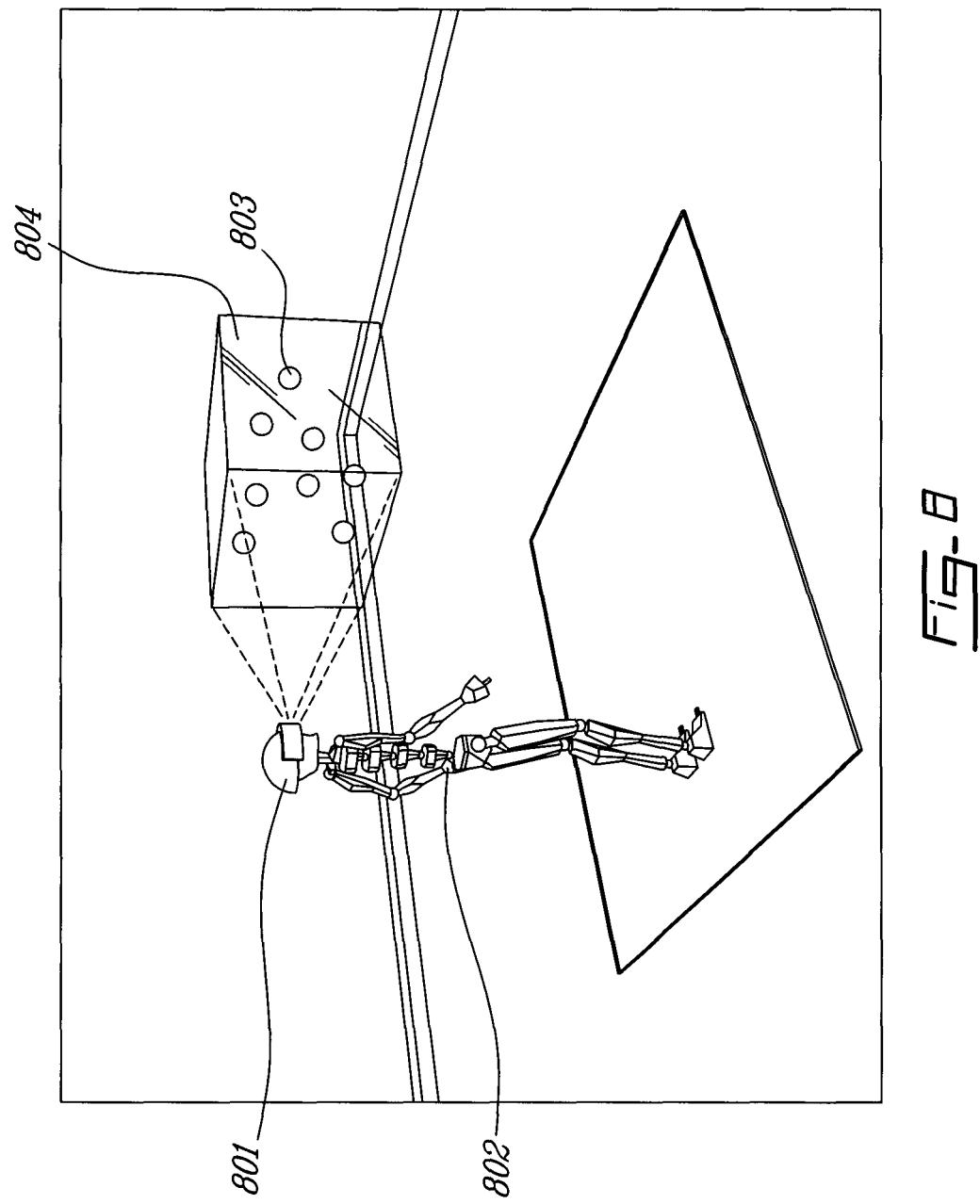
FIG. 8 is a perspective view of a system for 3D visual immersion.

Referring to FIG. 8, Embodiment 2 relates to a method and system for assessing, training and improving perceptual-cognitive abilities of athletes and other populations.

Embodiment 2 relates to a method and system using as display a virtual reality visual implement, for example a virtual reality helmet 801 and a MOT procedure using variation of speed for evaluating and training the perceptual-cognitive capacity of athletes and other target populations.

The method and system according to Embodiment 2 uses a virtual three-dimensional environment to evaluate and train the perceptual-cognitive abilities of a subject. The three-dimensional environment and situations being proposed can be adapted to the specificities of the target population. Examples of three-dimensional environments are illustrated in FIG. 8 (moving balls), FIG. 9 (Football), FIG. 10 (Football) and FIG. 11 (Soccer).

Referring to FIG. 8, the virtual reality helmet 801 is connected to a display controller, for example a computer (not shown). The display controller is connected to the virtual reality helmet 801 for displaying through the virtual reality helmet 801 a 3D image of the virtual three-dimensional environment as a function of the orientation of the helmet 801 and in such a manner that the subject 802 has the impression of being immersed in the virtual three-dimensional environment corresponding to the MOT procedure.

The three-dimensional environment of FIG. 8 corresponds to Embodiment 1 as described in the foregoing description but conducted through the virtual reality helmet 801 and corresponding display controller (computer). As described herein above, this procedure consists of displaying a 3D set of eight (8) spheres such as 803 in a transparent 3D volume 804 and identifying at least one sphere 803 as target through a brief change of colour (from yellow to red for example). The subject 802 then visually tracks the at least one identified target sphere 803 within the volume 804 while the spheres 803 move and are allowed to collide with each other and on the six planar surface boundaries of the parallelepiped delimiting the 3D volume 804. At the end of the exercise, all the spheres 803 are identified by numbers and the subject 802 indicates the at least one target sphere that has been tracked, by indicating the number of that sphere.

Figure 9:
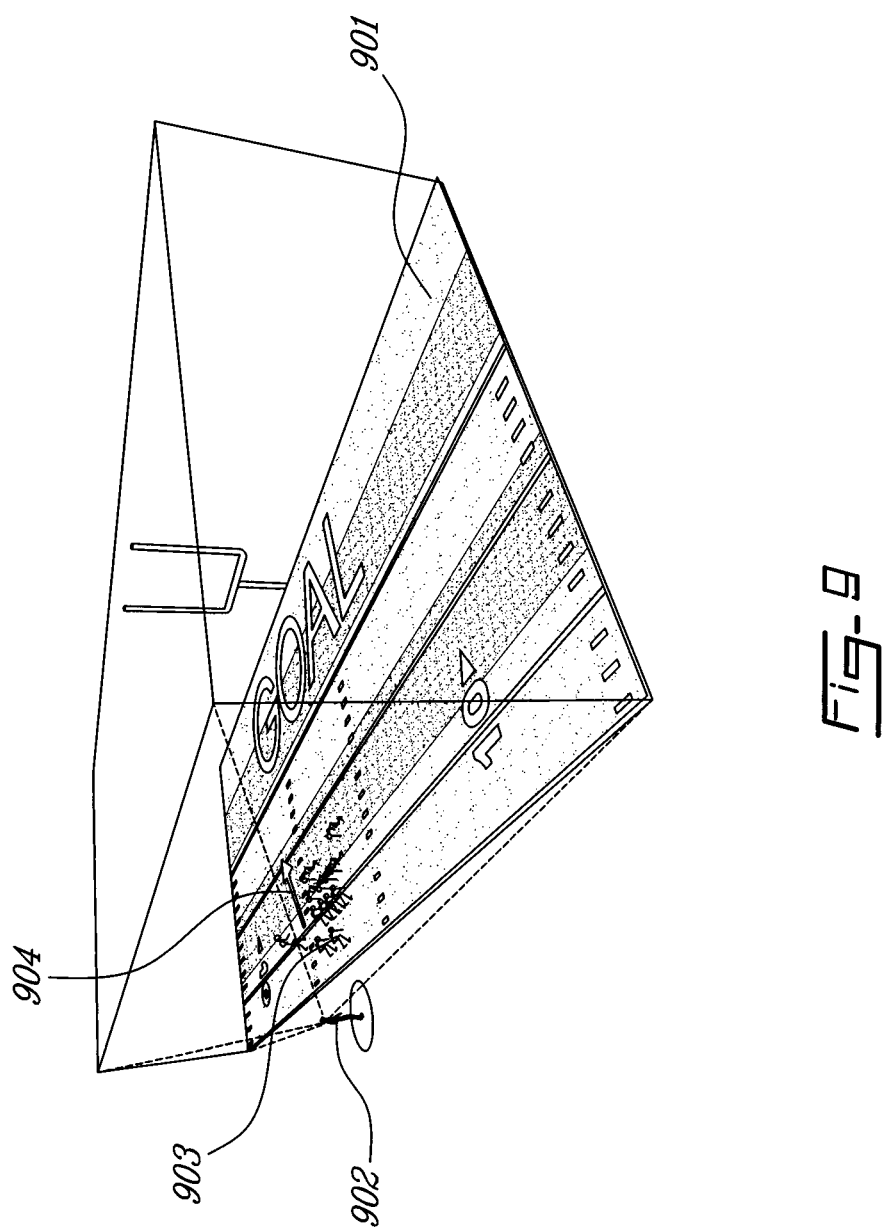
FIG. 9 is a perspective view of a system for 3D visual immersion in a football playground.
Figure 10:
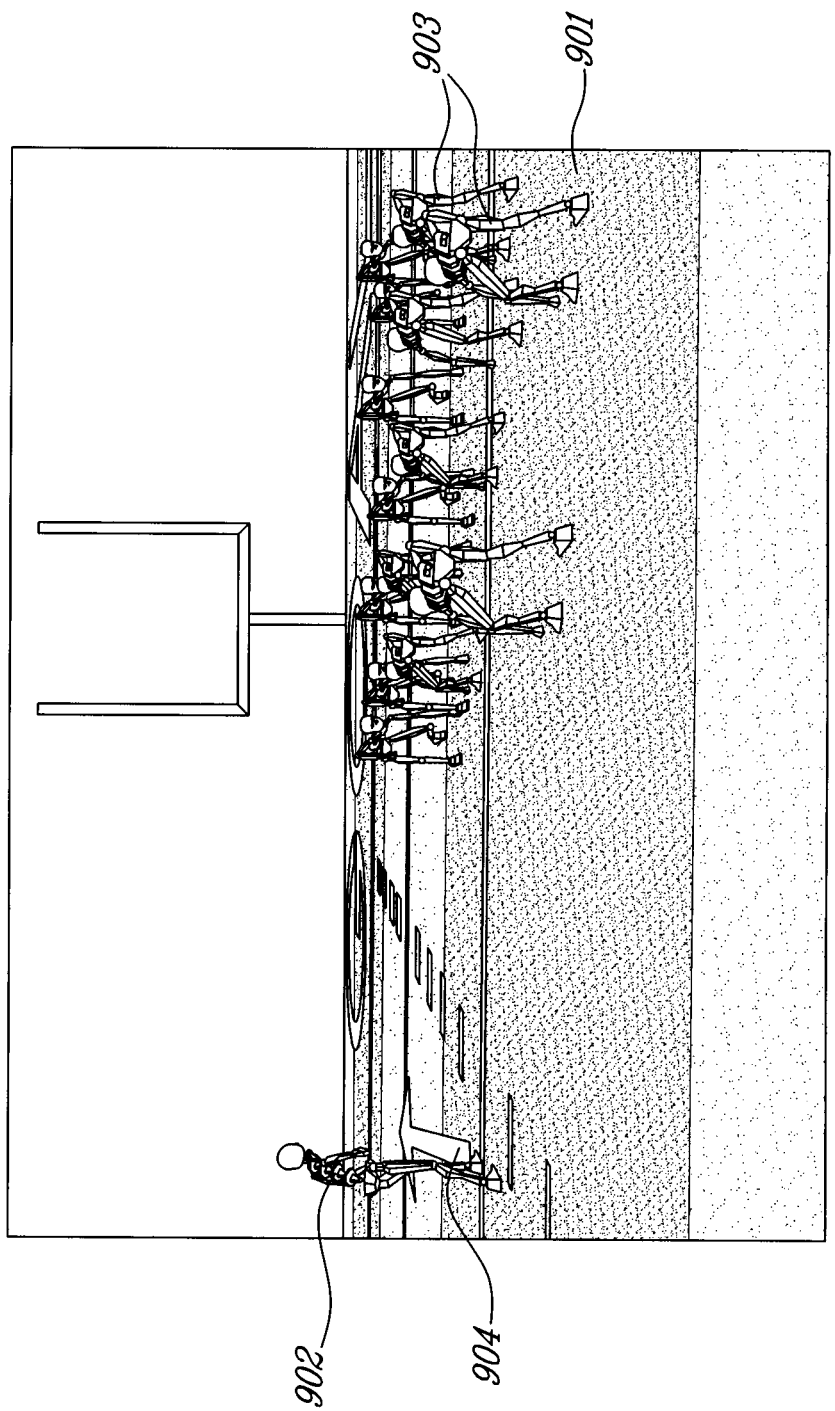
FIG. 10 is an elevation view of a scene as seen by a subject during visual immersion using the system of FIG. 9.
Figure 11:
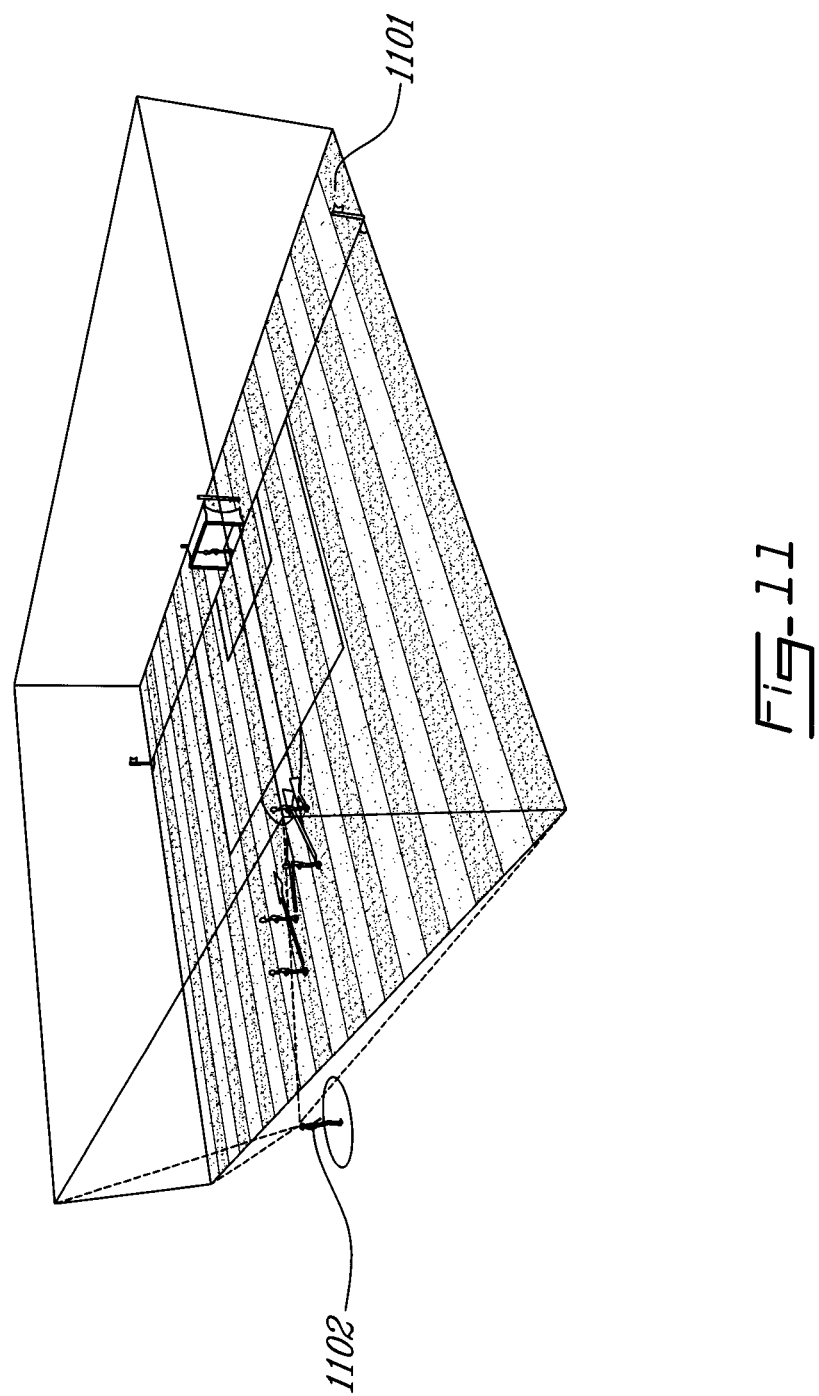
FIG. 11 is a perspective view of a system for 3D visual immersion in a soccer playground.

The virtual three-dimensional environment of FIG. 9 is a football playground 901 and the virtual three-dimensional environment of FIG. 11 is a soccer playground 1101 both displayed through the virtual reality helmet 801. The moving virtual objects can then be a ball and/or football or soccer players. FIG. 10 shows the 3D image of the football playground 901 as seen by the subject 902 of FIG. 9 through the virtual reality helmet 801.

In the case of the football playground 901 of FIGS. 9 and 10, football players 903 appear in the 3D image (FIG. 10) as seen by the subject 902 through the virtual reality helmet 801. The display controller can control the virtual reality helmet 801 to display indications, such as arrows (904, for example), to indicate to the subject 902 a movement that can be anticipated from one or many players during a play to come.

Then, the play is started and the players 903 and ball (not shown) will move on the football playground 901 and the exercise of the subject 902 is to observe the play and movements of the players 903 and ball. The display controller can also control the virtual reality helmet to change the speed of the play from one play to the other, for example to increase the speed from one play to the other. This will provide to the subject 902 an exercise and training to observe and get acquainted of, during a play, the simultaneous movements of the players and ball. To improve the perceptual-cognitive abilities of the subject 902, the speed can be gradually increased from on play to the other. This will allow to improve the speed of the play up to a level that, when the subject 902 will face a real situation or play during a football game, he will find movements of the players and ball slow and he will be faster to anticipate a play or determine the current movements and positions of the other player to better react, take faster decisions and ultimately improves his performance in playing football.

The same applies to the environment (soccer playground 1101 of FIG. 11) to allow a subject 1102 to practice and increase the speed at which he/she will be able to anticipate a play and determine the current movements and positions of the other players to better react, take faster decisions and ultimately improves his performance in playing soccer.

The perceptual-cognitive abilities of athletes and of the population in general are fundamental in their interaction with their environment. The above method and system of Embodiment 2 will enable to evaluate and train perceptual-cognitive abilities of individuals in many daily tasks such as driving a car and practicing sports. More specifically, this solution will be very efficient to evaluate and optimize the ability of an individual to interact with the surrounding, complex dynamic environment. For example, this type of tool could be used to determine the profile of a driver and evaluate whether his/her perceptual-cognitive abilities are optimal and sufficient to ensure safety in the traffic. It will also be possible, as described hereinabove in relation to Embodiment 1, to conceive a protocol to evaluate the perceptual-cognitive abilities of athletes and then, as a function of this evaluation, to elaborate a training program for these athletes. In particular, this procedure or protocol will evaluate the response of the subjects to the particular events or situation as a function of the speed of movement of the virtual objects in the environment. A suitable collector (not shown) of the responses of concern from the subject can be easily designed by those of ordinary skill in the art as a function of the protocol being used.

For example, in the area of sports, various organizations are constantly searching for new efficient tools for training high-level athletes in view of optimizing their performance. The method and system of Embodiment 2 constitutes a new alternative to the development of the performance of athletes. They can also be adapted to many other situations for example a profession requiring a high perceptual-cognitive efficiency within a complex dynamic environment to take fast and efficient decisions, for example during the training of SWAT teams and elite corps fighting against terrorism.

The method and system of Embodiment 2 can be applied as well in the context of re-adaptation of the perceptual-cognitive abilities.

The method and system of Embodiment 2 comprises, amongst others, the following advantages:

The method and system of Embodiment 2 are capable of determining precisely the level of the perceptual-cognitive performance of an individual.

The realism provided by the virtual reality permits a better transfer to the real world.

The system of Embodiment 2 is portable and can be transported on a training site, for example on a playground.

The method and system of Embodiment 2 is simple to use.

The method and system of Embodiment 2 are capable of measuring the perceptual-cognitive abilities of an individual in visual conditions reproducing the visual reality of the environment (3D visual immersion).

The method and system of Embodiment 2 are capable of measuring precisely the perceptual-cognitive abilities of an individual in a virtual environment reproducing in a realistic manner the visual requirements inherent to the practice of a sport.

The method and system of Embodiment 2 (FIG. 8) can be used to train elders to process the moving virtual spheres 804 as well as untrained young adults:

Normal aging is associated with a decline of perceptual-cognitive abilities. Aging is also know to affect motion perception and divided attention. For example, young subjects can simultaneously track four (4) moving objects while older subjects can only track three (3) moving objects simultaneously. It has been demonstrated that, using the embodiment of FIG. 8, the perceptual-cognitive abilities in a 3D-MOT task are trainable over time, and trained older subjects can become as efficient as untrained younger subjects. The method and system of Embodiment 2 (FIG. 8) is therefore a useful technique in aging to reduce the impact of perceptual-cognitive decline.

Embodiment 3

Augmented Reality

In Embodiment 3, the above described Embodiment 2 is extended to augmented reality. Embodiment 3 still relates to a method and system for assessing, training and improving perceptual-cognitive abilities of athletes and other populations.

Figure 12:
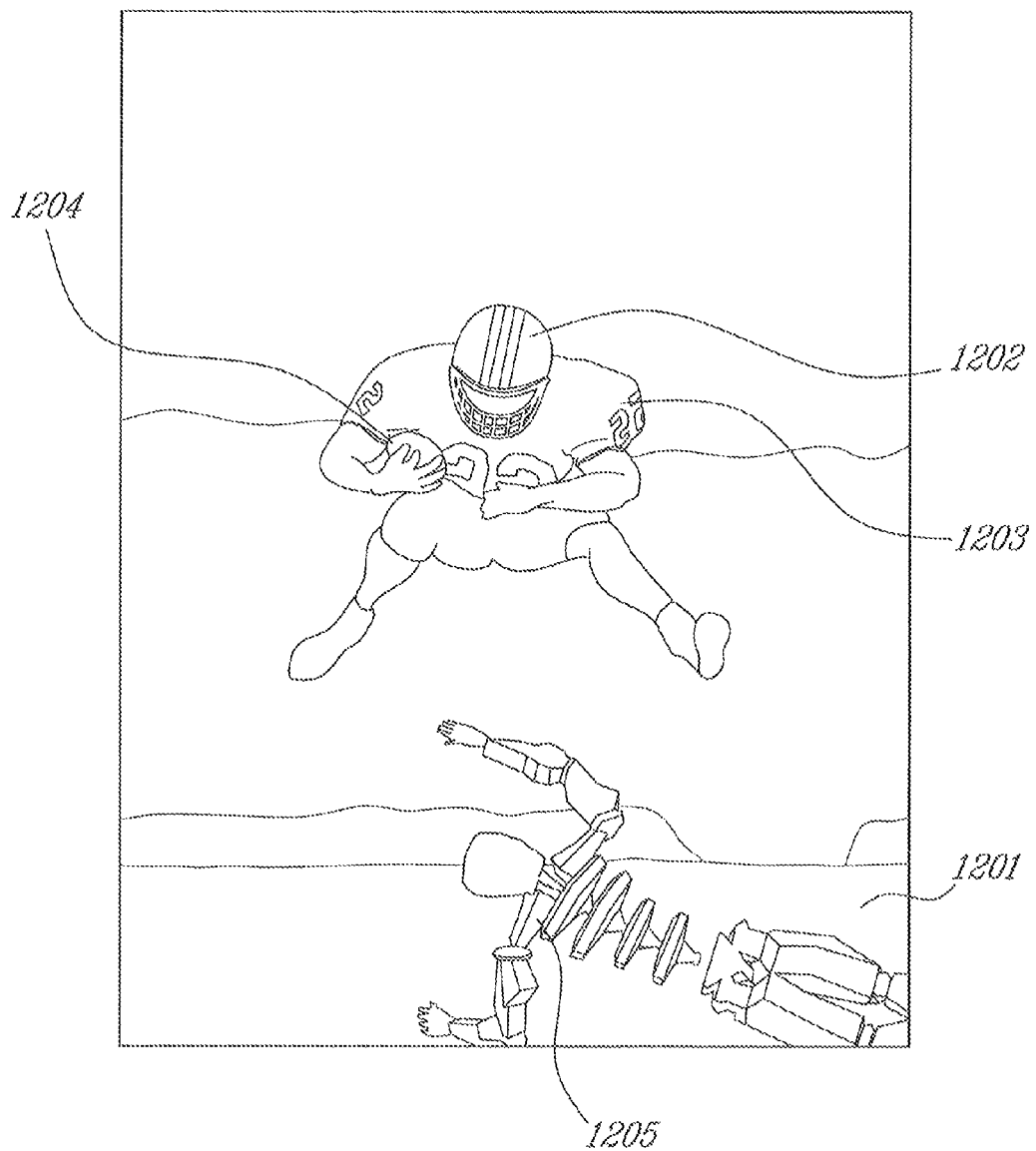
FIG. 12 is an illustration of a system for 3D augmented reality used in relation to a football playground.

More specifically, the method and system according to Embodiment 3 allow a subject 1203 to be in a real three-dimensional environment, for example a football playground 1201 as illustrated in FIG. 12. The display then comprises a virtual reality visual implement, for example a virtual reality helmet 1202, glasses or any other virtual reality visual implement. A display controller, for example a computer (not shown), is connected to the virtual reality helmet 1202 to the virtual reality helmet 1202 through a wireless connection (not shown) to display and superimpose in 3D virtual objects to the real football playground 1201. The 3D virtual objects are selected from the group consisting of football players such as 1205 and a ball such as 1204.

In the case of augmented reality, the virtual reality helmet 1202 is structured to allow the subject 1203 to see the real football playground 1201 and the 3D virtual objects superimposed to the real football playground 1201 whereby the subject can move, change direction, run, jump, etc. on the real football playground 1201 while the 3D virtual objects are stationary or move on the real football playground 1201. To augment the reality, the display controller controls the virtual reality helmet 1202 to display in three dimensions objects such as other players such as 1205 and a ball such as 1204 stationary or moving on the football playground 1201. Alternatively, the ball 1204 can be real and carried by the subject 1203.

For example, the subject 1203 can run on the football playground 1201 towards the score line (not shown). During movement of the subject 1203, the display controller will control the virtual reality helmet 1202 to display 3D players 1205 trying to stop the subject 1203. The subject 1203 will then run, change direction and/or jump to avoid the other players such as 1205 in an attempt to reach the score line.

In Embodiment 3, the collector of responses from the subject 1203 may comprise sensors (not shown) mounted on the subject 1203 and connected to a computer. The sensors detect the movements and position of the subject 1203 on the real football playground 1201 for use by the computer for evaluating, according to an evaluation protocol, the perceptual-cognitive abilities of the subject 1203.

This will allow the subject 1203 not only to observe the play and movements of the players 1205 and ball 1204 but also to move on the football playground 1201 as a function of the movements and positions of the other players 1205 and ball 1204. This will provide to the subject 1203 an exercise and training not only to observe and get acquainted of, during a play, the simultaneous movements of the players 1205 and ball 1204 but also to play, i.e. to take fast decisions and move in relation to the acquired information and the decisions taken. To improve the perceptual-cognitive abilities of the subject 1203, the display controller can control the virtual reality helmet 1202 to gradually increase the speed of the play from one play to the other. It is possible to increase the speed of the play up to a level that, when the subject 1203 will face a real situation or play during a football game, he/she will find movements of the players and ball slow and he will be faster to anticipate a play or determine the current movements and positions of the other player(s) to better react, take faster decisions and ultimately improve his/her performance in playing football.

The same may apply to other real three-dimensional environments such as a boxing ring 1301 as illustrated in FIG. 13. In this particular situation, a subject 1302 will fight in a real three-dimensional boxing ring 1301 against a virtual adversary 1303 to practice and increase the speed at which he will be able to anticipate a movement of the virtual adversary 1303 and better and faster respond by trying to hit the virtual adversary 1303. In FIG. 13, the virtual reality helmet of the subject 1302 is not shown.

Results

FIG. 14 is a graph showing that the perceptual-cognitive abilities of subjects improve when a 3D-stereoscopic representation of the virtual objects is used. The graph of FIG. 14 also shows that the perceptual-cognitive abilities are also better in the case of subjects not suffering from visual amblyopia.

The curve of FIG. 15 clearly shows that the perceptual-cognitive abilities of subjects improve with the number of training sessions.

It is to be understood that the invention is not limited in its application to the details of construction and parts illustrated in the accompanying drawings and described hereinabove. The invention is capable of other embodiments and of being practiced in various ways. It is also to be understood that the phraseology or terminology used herein is for the purpose of description and not limitation. Hence, although the present invention has been described hereinabove by way of illustrative embodiments thereof, it can be modified at will, within the scope of the appended claims, without departing from the spirit, scope and nature of the subject invention.

What is claimed is:

1. A device for evaluating or improving perceptual-cognitive abilities of a subject, comprising:
at least one sensor adapted to detect a movement and a position of the subject within a real, physical three-dimensional environment;
a display apparatus comprising an augmented reality helmet configured to display stereoscopic images of moving virtual objects superimposed on the real, physical three-dimensional environment, the virtual objects being displayed during a sequence of successive tests in a manner allowing the subject to be in visual contact with the virtual objects while the subject is moving within the real, physical three-dimensional environment, the display apparatus being adapted to detect an orientation of the augmented reality helmet; and
a controller adapted to:
control the display apparatus to correct in real-time a subject's visual perspective based on the detected orientation of the augmented reality helmet;
evaluate, according to an evaluation protocol, the perceptual-cognitive abilities of the subject as a function of the movement and of the position of the subject within the real, physical three-dimensional environment in response to the moving virtual objects superimposed on the real, physical three-dimensional environment; and
change, during the sequence of the successive tests, a speed of movement of the virtual objects displayed by the display apparatus using a staircase variation to increase or decrease the speed of the virtual objects, based on the evaluation of the perceptual-cognitive abilities of the subject from at least one preceding successive test in the sequence of successive tests.

2. A device as defined in claim 1, further comprising a collector of responses configured to receive from the subject responses to the successive tests for use in evaluating, according to the evaluation protocol, the perceptual-cognitive abilities of the subject.

3. A device as defined in claim 2, wherein the collector of responses comprises one of the following devices:
a computer in which verbal responses from the subject are entered for each of the successive tests for evaluating, according to the evaluation protocol, the perceptual-cognitive abilities of the subject;
a keyboard operable by the subject to enter the responses to the successive tests in a computer for evaluating, according to the evaluation protocol, the perceptual-cognitive abilities of the subject; and
a voice recognition system adapted to enter the responses from the subject to the successive tests in a computer for evaluating, according to the evaluation protocol, the perceptual-cognitive abilities of the subject.

4. A device as defined in claim 2, further comprising, following a response phase in which the collector of responses receives the responses from the subject, a feedback phase in which target objects are identified to give a feedback to the subject.

5. A device as defined in claim 2, wherein the controller is configured to control the display apparatus to execute, during each test, the following sequence of phases:
a presentation phase in which the virtual objects are displayed in random positions on the display apparatus;
an indexation phase in which a portion of the virtual objects displayed in the presentation phase are identified as target objects; and
a tracking phase in which the virtual objects move; and
a response phase in which tracking responses related to the target objects are received on the collector of responses.

6. A device as defined in claim 1, wherein:
the augmented reality helmet comprises a shutter visual implement.

7. A device as defined in claim 1, wherein:
the real, physical three-dimensional environment is a sport playground visible through the augmented reality helmet,
the virtual objects are selected from the group consisting of players and a ball, and
the controller is configured to control the display apparatus to change a speed of a play from one play to the other.

8. A device as defined in claim 1, further comprising:
a collector of responses configured to receive from the subject responses to the successive tests for use in the evaluation of the perceptual-cognitive abilities of the subject,
wherein the real, physical three-dimensional environment is a real sport playground, wherein the moving virtual objects are three-dimensional virtual objects selected from the group consisting of players and a ball, wherein the augmented reality helmet is structured to present to the subject the real sport playground and the three-dimensional virtual objects superimposed to the real sport playground, wherein the collector of responses comprises sensors mounted on the subject and connected to a computer, and wherein the sensors detect movements and position of the subject on the real sport playground for use by the computer for the evaluation of the perceptual-cognitive abilities of the subject.

9. A device as defined in claim 1, wherein, to produce the staircase variation of the speed of movement of the virtual objects, the controller:
increases the speed of movement of the virtual objects by a factor of 0.2 log unit following a correct identification of the moving virtual objects by the subject after a given one of the successive tests; and
decreases the speed of movement of the virtual objects by a factor of 0.2 log unit following an incorrect identification of the moving virtual objects by the subject after the given one of the successive tests.

10. A method of evaluating or improving perceptual-cognitive abilities of a subject, comprising:
detecting a movement and a position of the subject within a real, physical three-dimensional environment;
displaying, on a display apparatus, moving virtual objects superimposed on the real, physical three-dimensional environment during a sequence of successive tests, the display apparatus comprising an augmented reality helmet configured to display stereoscopic images of the virtual objects in a manner allowing the subject to be in visual contact with the virtual objects while the subject is moving within the real, physical three-dimensional environment, the display apparatus being adapted to detect an orientation of the augmented reality helmet;
controlling the display apparatus to correct in real-time a visual perspective based on the detected orientation of the augmented reality helmet;
evaluating, according to an evaluation protocol, the perceptual-cognitive abilities of the subject as a function of the movement and of the position of the subject within the real, physical three-dimensional environment in response to the moving virtual objects superimposed on the real, physical three-dimensional environment; and changing, during the sequence of the successive tests, a speed of movement of the virtual objects displayed by the display apparatus using a staircase variation to increase or decrease the speed of the virtual objects, based on the evaluation of the perceptual-cognitive abilities of the subject from at least one preceding successive test in the sequence of successive tests.

11. A method as defined in claim 10, further comprising collecting responses from the subject to the successive tests for use in the evaluation of the perceptual-cognitive abilities of the subject.

12. A method as defined in claim 11, further comprising, following a response phase in which the responses from the subject are collected, a feedback phase in which the target objects are identified to give a feedback to the subject.

13. A method as defined in claim 10, wherein changing the speed of movement of the virtual objects comprises moving the virtual objects at a constant speed during each test, and changing the speed of movement of the virtual objects from one of the successive tests to the other.

14. A method as defined in claim 10, wherein changing the speed of movement of the virtual objects comprises adjusting the speed of movement of the virtual objects in relation to responses from the subject to the successive tests.

15. A method as defined in claim 10, wherein the evaluation protocol evaluates responses from the subject to the successive tests as a function of the speed of movement of the virtual objects in the real, physical three-dimensional environment.

16. A method as defined in claim 10, wherein displaying the moving virtual objects comprises executing, during each test, the following sequence of phases:

a presentation phase in which the virtual objects are presented in random positions to the subject;

an indexation phase in which a portion of the virtual objects presented in the presentation phase are identified as target objects; and a tracking phase in which the virtual objects move and the target objects are tracked by the subject for a predetermined duration; and a response phase in which the subject identifies, as response to the test, the target objects.

* * * * *